US00PP23454P2

(12) United States Plant Patent
Oliver

(10) Patent No.: US PP23,454 P2
(45) Date of Patent: Mar. 5, 2013

(54) ***HEUCHERA* PLANT NAMED 'DARK CHOCOLATE'**

(50) Latin Name: *Heuchera*
Varietal Denomination: Dark Chocolate

(75) Inventor: Charles Oliver, Scottdale, PA (US)

(73) Assignee: Plants Nouveau LLC., Charleston, SC (US)

( * ) Notice: Subject to any disclaimer, the term of this patent is extended or adjusted under 35 U.S.C. 154(b) by 34 days.

(21) Appl. No.: 13/136,148

(22) Filed: Jul. 25, 2011

(51) Int. Cl.
*A01H 5/00* (2006.01)

(52) U.S. Cl. ..... Plt./440
(58) Field of Classification Search ..... Plt./440
See application file for complete search history.

*Primary Examiner* — Susan McCormick Ewoldt
(74) *Attorney, Agent, or Firm* — Penny J. Aguirre

(57) ABSTRACT

A new cultivar of *Heuchera* of hybrid origin, 'Dark Chocolate', that is characterized by its foliage that is dark purple-bronze that is overlaid with silvery green mottling with the coloration retained throughout the growing season, its flowers that are comparatively large, well shaped, and pink in color, its red-purple flower buds and red-purple stems that contrast well with its pink flowers, its well-proportioned plant form, its foliage that is weather resistant with good tolerance to wind and rain, and its good garden performance.

2 Drawing Sheets

Botanical classification: *Heuchera* hybrid.
Cultivar designation: 'Dark Chocolate'.

BACKGROUND OF THE INVENTION

The present invention relates to a new and distinct cultivar of hybrid *Heuchera*, botanically known as a *Heuchera* of hybrid origin and is hereinafter referred to by the cultivar name 'Dark Chocolate'.

The new cultivar derived from a controlled breeding program conducted by the inventor in Scottsdale, Pa. The goal of the breeding program was to obtain unique cultivars of *Heuchera* that exhibit showy flowers, colorful foliage, and good vigor. The inventor made a cross in may 2004 between an unnamed plant from the inventor's breeding program as the female parent, reference no. H01-16A, and 'Caroline' (U.S. Plant Pat. No. 20,026) as the male parent. 'Dark Chocolate' was selected as a single unique plant in May 2005 amongst the seedlings that resulted from the above cross.

Asexual reproduction of the new cultivar was first accomplished by division in Scottsdale, Pa. in October 2007. Asexual reproduction of the new cultivar by division, cuttings, and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Dark Chocolate' as a new and unique cultivar of *Heuchera*.

1. 'Dark Chocolate' exhibits foliage that is dark purple-bronze and overlaid with silvery green mottling with the coloration retained throughout the growing season.
2. 'Dark Chocolate' exhibits flowers that are comparatively large, well shaped, and pink in color.
3. 'Dark Chocolate' exhibits red-purple flower buds and red-purple stems that contrast well with its pink flowers.
4. 'Dark Chocolate' exhibits a well-proportioned plant form.

5. 'Dark Chocolate' exhibits evergreen foliage that is weather resistant with good tolerance to wind and rain.
6. 'Dark Chocolate' exhibits good garden performance.

'Dark Chocolate' can be readily distinguished from its parent plants. The female parent, H01-16A, differs from 'Dark Chocolate' in having foliage that is loses its purple coloration by the end of the blooming season and becomes bronzy green, in having foliage that lacks silver mottling, and in having wider and more open flower panicles. The male parent, 'Caroline' differs from 'Dark Chocolate' in having in having foliage that is loses its purple coloration by the end of the blooming season and becomes bronzy green, in having longer petioles, in having more outward facing and smaller flowers, in having flower petals that have dentated margins rather than entire, and in having peduncles that are longer but with shorter panicles.

'Dark Chocolate' can be compared most closely compared to the cultivar 'Harmonic Convergence' (U.S. Plant Pat. No. 11,111). 'Harmonic Convergence' differs from 'Dark Chocolate' in having leaves that are less rounded (more angular) with basal lobes that are not overlapping, in having inflorescences that are more conical in shape (wider base) and branched into 2 to 3 panicles, and in having flowers that smaller in size with petals that are white in color, lack glandular hairs, are recurved, and have styles that are exserted. 'Dark Chocolate' can be compared to 'Stainless Steel' (U.S. Plant patent application Ser. No. 13/136,164). 'Stainless Steel' is similar in having flowers that are comparatively large and well shaped, in having evergreen foliage that is weather resistant with good tolerance to wind and rain, and in having good garden performance. 'Stainless Steel' differs from 'Dark Chocolate' in having foliage that emerges silver in color and heavily suffused with red-purple that matures to silver with green veins and in having flowers that are white in color.

BRIEF DESCRIPTION OF THE DRAWING

The accompanying colored photographs illustrate the overall appearance and distinct characteristics of the new *Heuchera*.

The photograph in FIG. 1 was taken of a two-year old plant as grown in a greenhouse in Scottsdale, Pa. and provides a side view of a 'Dark Chocolate' in bloom.

Figure 1:
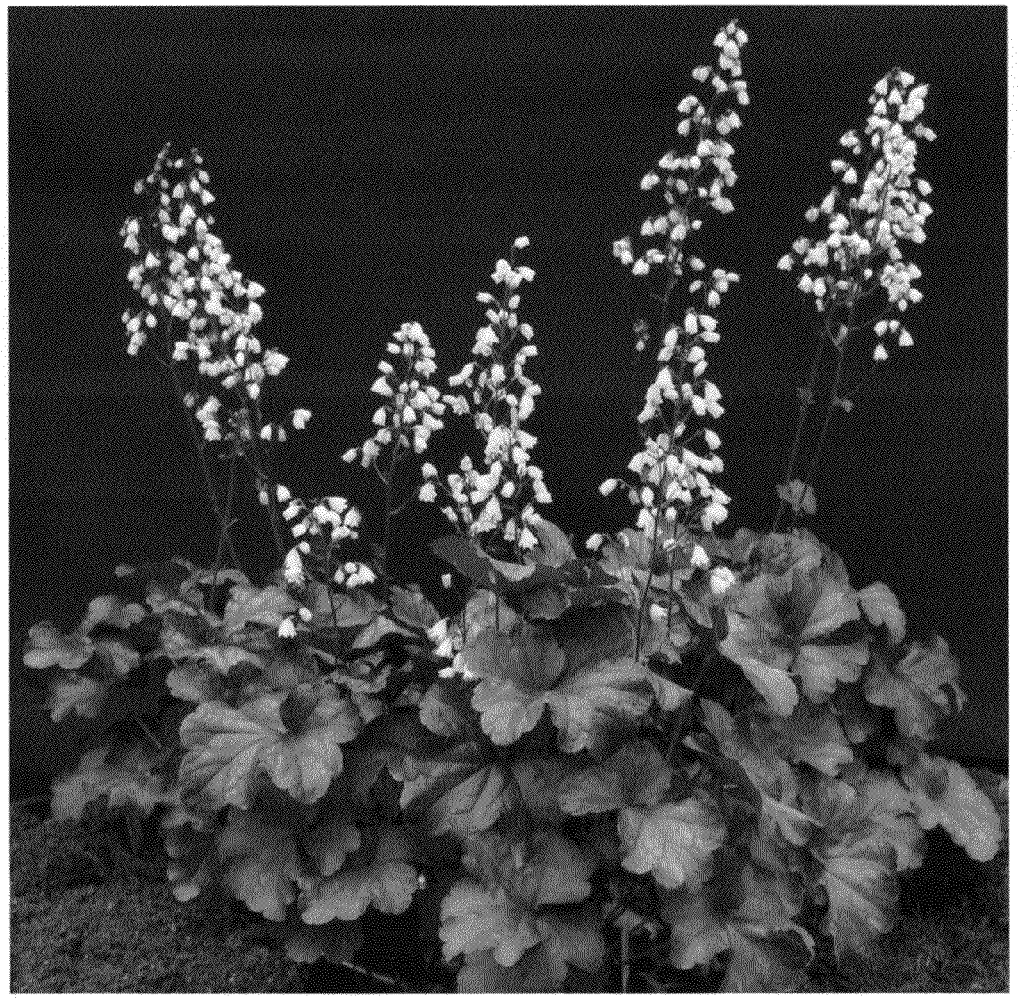
Figure 2:
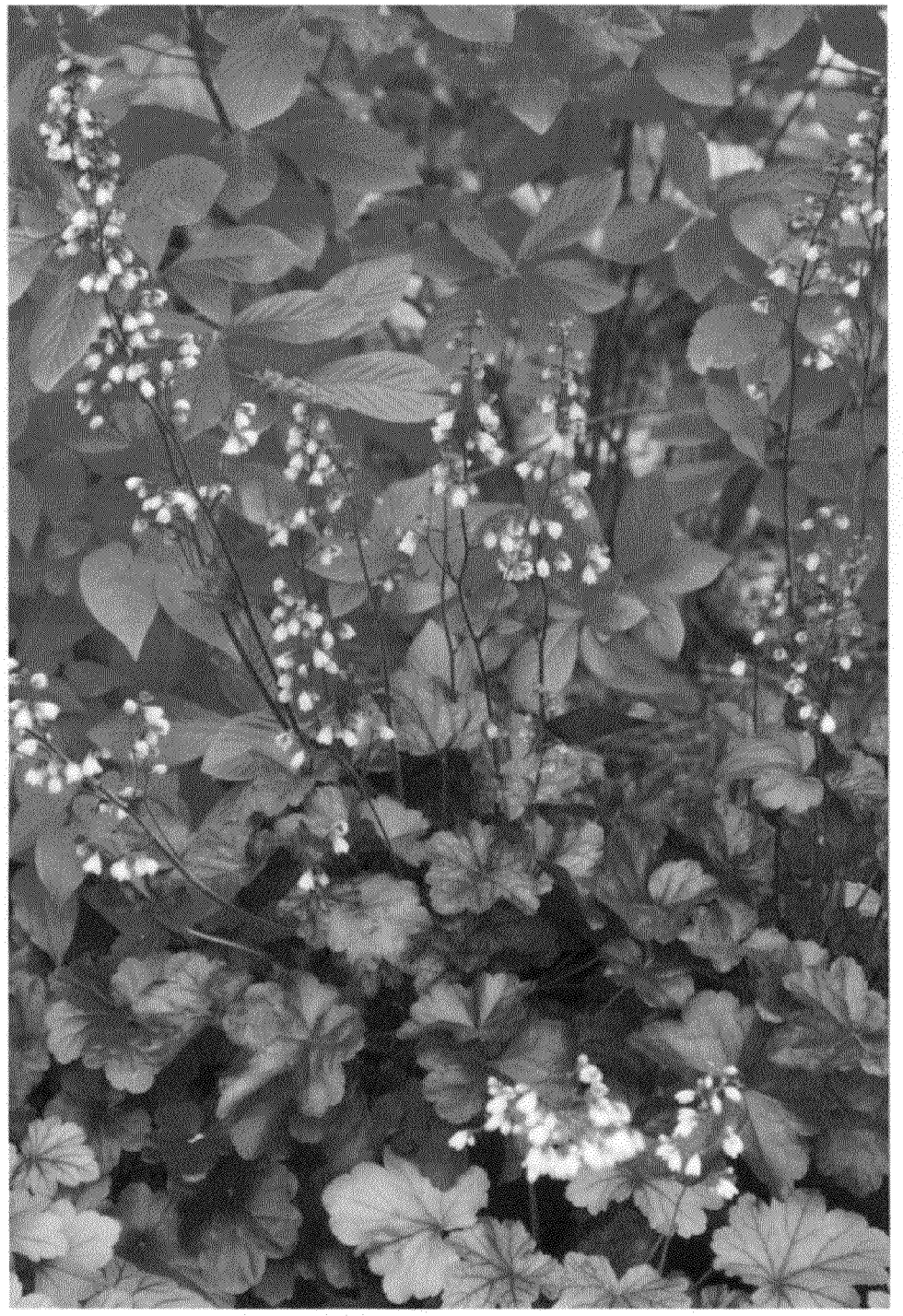

The photograph in FIG. 2 was taken of a two-year old plant as grown in a garden in Baltimore, Md. and provides a side view of a 'Dark Chocolate' in bloom. The colors in the photograph may differ slightly from the color values cited in the detailed botanical description, which accurately describe the colors of the new *Heuchera*.

DETAILED BOTANICAL DESCRIPTION OF THE PLANT

The following is a detailed description of one year-old plants of the new cultivar as grown in one-gallon containers in a glass greenhouse in Scottsdale, Pa. The plants were grown under average day temperatures of 26° (summer) to 15° C. (winter) and average night temperatures of 15° (summer) to 5° C. (winter). The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Herbaceous perennial.

*Plant habit*.—Clump-forming, mounded evergreen foliage.

*Height and spread*.—Average of 35 to 45 cm in height in bloom with foliage height about 15 cm and a spread of 30 to 40 cm.

*Blooming period*.—May to June in Scottsdale, Pa.

*Hardiness*.—At least tolerant between −30° C. and 45° C.

*Diseases and pests*.—Disease free in the conditions tested, no susceptibility or resistance to pests has been observed.

*Environmental stresses*.—Excellent tolerance to rain and wind.

*Root description*.—Finely fibrous roots on woody rootstalks.

*Branching habit*.—Basal rosettes.

*Propagation*.—Cuttings and tissue culture preferred.

*Root initiation*.—Roots appear in rooting media in 15 days at 23° C. in summer and in 21 days at 17° C. in winter.

*Root development*.—Rooted cuttings or liners develop in 45 days at 23° C. and in 60 days at 17° C.

*Growth rate*.—Vigorous.

Foliage description:

*Leaf shape*.—Rounded-cordate.

*Leaf division*.—Simple.

*Leaf base*.—Auriculate.

*Leaf apex*.—Broadly obtuse.

*Leaf venation*.—Reticulate, color; upper surface; 198A underlain by 200A, lower surface; 187A.

*Leaf margins*.—Lobed with lobe margins ciliate and crenate.

*Leaf attachment*.—Petiolate.

*Leaf arrangement*.—Rosettes.

*Leaf orientation*.—Held horizontal to petiole, slightly wavy.

*Leaf surface*.—Slightly rough texture, slightly pubescent on upper and lower surface.

*Leaf color*.—Young and mature upper surface; 187A and overlaid with mottling of 198B, young and mature lower surface; 187A, coloration is retained throughout the summer.

*Leaf size*.—Average of 9 cm in length and 8 cm in width.

*Petioles*.—Round in shape, average of 12 cm in length, average of 1.8 mm in diameter, 187B in color, surface is slightly pubescent.

Flower description:

*Inflorescence type*.—Numerous small bell-shaped flowers arranged on narrow cylindrical panicles.

*Inflorescence size*.—Average of 35 to 45 cm in height and an average of 5 to 7 cm in width.

*Flower fragrance*.—None.

*Flower quantity*.—8 to 10 per basal peduncles, 1 to 2 at terminus, average of 100 to 150 per flowering stem.

*Flower lastingness*.—Average of 7 days per flower, individual panicles bloom for about 2 weeks, flowers persistent.

*Flower buds*.—Obovate in shape, average of 4 mm in diameter and 3 mm in depth, 59C in color.

*Flower aspect*.—Held slightly downward (drooping) on pedicels held at about a 45° angle from peduncle.

*Flower shape*.—Campanulate in shape.

*Flower size*.—Average of 8 mm in diameter and depth.

*Petals*.—5, spatulate in shape and not recurved, margin is entire, apex is obtuse, about 4.5 mm in length and 2 mm in width, upper surface is smooth and lower surface has glandular hairs, color; upper surface when opening; NN155B, lower surface; NN155B when opening with glandular hairs 62A, upper surface when fully open; NN155B, lower surface when fully open; NN155B with glandular hairs 62A.

*Calyx*.—Campanulate in shape, 8 mm in length and diameter.

*Sepals*.—5, un-fused portion is broadly oblong in shape, average of 8 mm in length and 2.5 mm in width, margin is entire, apex is obtuse, base is fused, upper surface 62A in color with glandular hairs on the distal portion, lower surface 62A in color heavily suffused with glandular hairs 62A in color, surface is pubescent on upper and lower surface.

*Rachis* (*flower scape*).—Strong, average of 40 cm in length and 2 mm in diameter, surface covered with glandular hairs, 187B in color, held at about a 90° angle.

*Peduncles*.—Strong, average of 1 cm in length and 0.5 mm in diameter, surface covered with glandular hairs, 187B in color, held at about a 45° angle.

*Pedicels*.—Strong, average of 3 mm in length and 0.2 mm in width, surface pubescent with glandular hairs, 194B with glandular hairs 187B in color, held at about a 60° angle.

*Bracts*.—Average of 4 mm in length and 1 mm in width, lanceolate in shape, margin is serrate, apex is acute, surface is pubescent with glandular hairs, upper and lower surface 187B in color.

Reproductive organs:

*Gynoecium*.—2 Pistils, about 6 mm in length, stigmas round in shape and 157A in color, styles are not exerted, about 5 mm in length and 157D in color, ovary is 157D in color.

*Androcoecium*.—5 stamens, anthers are oval in shape, average of 0.6 mm to 1 mm in length and 25B in color, pollen is moderate in quantity and 25B in color.

*Seed*.—High in quantity, 0.6 mm in length, 0.3 mm in diameter, 203D in color.

It is claimed:

1. A new and distinct cultivar of *Heuchera* plant named 'Dark Chocolate' as herein illustrated and described.

* * * * *